United States Patent [19]

Soled et al.

[11] Patent Number: 4,518,707
[45] Date of Patent: May 21, 1985

[54] PROCESS FOR PREPARING HIGH SURFACE AREA IRON/COBALT FISCHER-TROPSCH SLURRY CATALYSTS

[75] Inventors: Stuart L. Soled, Madison; Rocco A. Fiato, Scotch Plains, both of N.J.

[73] Assignee: Exxon Research & Engineering Company, Florham Park, N.J.

[21] Appl. No.: 561,190

[22] Filed: Dec. 14, 1983

[51] Int. Cl.$^3$ .......................... B01J 23/78; B01J 27/22
[52] U.S. Cl. .................................. 502/174; 502/170; 502/177; 502/201; 502/217; 502/218; 502/224; 502/226; 502/328; 502/330; 502/524; 518/717
[58] Field of Search ............... 502/330, 524, 328, 177, 502/170, 174, 201, 217, 218, 224, 226; 518/717

[56] References Cited

U.S. PATENT DOCUMENTS

| | | | |
|---|---|---|---|
| 2,567,296 | 9/1951 | Milligan et al. | 502/330 |
| 2,662,090 | 12/1953 | Scharmann et al. | 260/449.6 |
| 2,686,195 | 8/1954 | McAdams et al. | 518/718 |
| 2,735,862 | 2/1956 | Buchmann et al. | 502/260 X |
| 2,850,515 | 9/1958 | Riblett | 260/449.6 |
| 4,154,751 | 5/1979 | McVicker et al. | 260/449.6 R |

FOREIGN PATENT DOCUMENTS 2050859A 1/1981 United Kingdom .

OTHER PUBLICATIONS

Khan et al., "The Synthesis of Light Hydrocarbons from CO and Hydrogen Mixtures over Selective Metal Catalysts", ACS 173rd Symposium, Fuel Div., New Orleans, (Mar. 1977), pp. 138–147.
Stud., Surf. Catal., 7, PT/A, p. 432, (1981).
"Mossbauer Spectroscopy of Supported Fe-Co Alloy Catalysts for Fischer-Tropsch Synthesis"–Journal of Catalysts, vol. 72, pp. 37–50, (1981).
"Mossbauer and Magnetic Studies of Bifunctional Medium-Pore Zeolite-Iron Catalysts Used in Synthesis Gas Conversion"–Advances in Chemistry Series, 1981, pp. 573–588, by Lo et al.
"Mossbauer Effect in Iron and Dilute Iron Based Alloys"–Physics Reports (Section C of Physics Letters), 12, No. 5, (1974), pp. 335–374.
Gmelins Handbuch der Anorganische Chemie, vol. 8, Auflage, (1959), pp. 408–413 and 1160–1161.
Hydrocarbon Processing, May 1983, pp. 88–96.
Chem-Ing.-Tech., 49, (1977), (No. 6: pp. 463–468, (1977), by D. Kitzelmann et al., German.
C.R. Acad. Sc. Paris, p. 268, (May 28, 1969), by P. Courty and B. Delmon.
"Fischer-Tropsch Synthesis with Iron-Cobalt Alloy Catalysts"–Stud. Surf. Sci. Catal., 7, Part A, pp. 432–446, (1981), (English).
AIChE, 1981, Summer National Meeting, Detroit, Preprint No. 408, (English).
Journal of Materials Science, 7, (1972), pp. 1383–1390, by A. C. C. Tseung and J. R. Goldstein.
ACS Meeting, Division of Petroleum Chemistry, Mar. 1978, entitled "Catalytic Synthesis of Light Olefinic Hydrocarbons from CO and Hydrogen Over Some Iron Catalysts", by C. H. Yang and A. G. Oblad.
Journal of Catalysis, 32, pp. 452–465, (1974), by J. R. Goldstein et al.
J. Phys. Chem. Solids 1959, vol. 9, pp. 165–175, by G. H. Jonker.
"The Fischer-Tropsch and Related Synthesis", by Storch, Golombic and Anderson, (Wiley), pp. 242–243.
Catal. Rev.-Syn. Eng., 21, (2), pp. 225–274, (1980).
J. Phys. Chem. Solids 1976, vol. 37, pp. 619–624, by P. J. Murray and J. W. Linnett.
"Numerical Data and Functional Relationships in Science and Technology", Landolt-Bornstein, New Series, vol. 12, part B, Magnetic and Other Properties of Oxides and Related Compounds: Spinels, Iron Oxides and Iron-Metal-Oxygen Compounds, editor K. H. Hellwege, pp. 245–250.
Kirk-Othmer, "Encyclopedia of Chemical Technology", 3rd Edition, vol. 13, pp. 90–95.
Journal of Catalysis, vol. 72, pp. 95–110, (1981), by J. A. Amelse, L. A. Schwartz and J. B. Butt.
Hydrocarbon Processing, Nov. 1980, pp. 139–142, "Make Olefins from Syn Gas", by V. U. S. Rao and R. J. Gormley.
Z. Physik Chemie Neue Folge, 112, 215–233, (1978), by Kitzelman et al., "In Situ Study of the Primary Reactions in the Hydrogenation of CO on Iron Catalysts".
J.C.S. Chem. Comm., pp. 428–430, (1983).

*Primary Examiner*—W. J. Shine
*Attorney, Agent, or Firm*—Robert J. North; Edward M. Corcoran

[57] ABSTRACT

Slurried high surface area Fe-Co spinels which are fully reduced/carburized provide exceptionally high activity and selectivity in the conversion of $CO/H_2$ to alpha-olefins. These iron-cobalt catalysts maintain good activity and selectivity under low pressure reaction conditions.

32 Claims, No Drawings

PROCESS FOR PREPARING HIGH SURFACE AREA IRON/COBALT FISCHER-TROPSCH SLURRY CATALYSTS

BACKGROUND OF THE INVENTION

1. Field of the Invention

This invention relates to high surface area iron-cobalt Fischer-Tropsch slurry catalysts, their preparation and use in Fischer-Tropsch slurry processes for selectively producing high amounts of $C_2$ to $C_{20}$ alpha-olefin materials.

2. Brief Description of the Prior Art

Methods for preparing low molecular weight olefins by Fischer-Tropsch processes using coprecipitated iron-based catalysts including cobalt as cocatalyst, are well-known in the art, as described, for example, in U.S. Pat. Nos. 2,850,515; 2,686,195; 2,662,090; and 2,735,862; AICHE 1981 Summer Nat'l Meeting Preprint No. 408, "The Synthesis of Light Hydrocarbons from CO and $H_2$ Mixtures over Selected Metal Catalysts" ACS 173rd Symposium, Fuel Division, New Orleans, March 1977; J. Catalysis 1981, No. 72(1), pp. 37–50; Adv. Chem. Sem. 1981, 194, 573–88; Physics Reports (Section C of Physics Letters) 12 No. 5 (1974) pp. 335–374; UK Patent Application No. 2050859A; J. Catalysis 72, 95–110 (1981); Gmelins Handbuch der Anorganische Chemie 8, Auflage (1959), pp 88–96; and Chem. Ing. Tech. 49 (1977) No. 6, pp. 463–468.

It is further known that high levels of cobalt in coprecipitated iron-cobalt alloy catalysts produce enhanced selectivity to olefinic products under certain process conditions, as described in Stud, Surf. Catal. 7, Pt/A, pp. 432 (1981).

Although the above-described prior art describes catalysts and processes displaying good fixed bed olefin synthesis activity, what is particularly desired are slurry catalysts which can preferably be completely pretreated in situ in the slurry liquid to yield the reduced, carbided active catalysts in the process displaying the combination of good $C_2$–$C_{20}$ olefin synthesis activity, low selectivity to methane, coupled with long-term activity maintenance which is essential for a successful commercial process. Particularly desired is where the catalyst precursor is the metal oxide spinel of the final catalyst composition.

It has been found that low surface area iron-cobalt spinels having BET surface areas below 5 $m^2/g$ are not readily pretreated in situ in a Fischer-Tropsch slurry liquid under mild conditions to readily yield active catalysts for producing $C_2$–$C_{20}$ olefins.

The preparation of high surface metal oxides is described in the French article, "C. R. Acad. Sc. Paris", p268 (May 28, 1969) by P. Courte and B. Delmon. The article describes a process for producing high surface area metal oxides by evaporating to dryness aqueous solutions of the corresponding glycolic acid, lactic acid, malic or tartaric acid metal salts. One oxide that was prepared by their described method was $CoFe_2O_4$.

However, the above references do not describe or suggest the use of single phase Fe:Co spinels having iron-cobalt atomic ratios of 4:1 or above or suggest their applicability in conducting or carrying out slurry-type Fischer-Tropsch processes.

SUMMARY OF THE INVENTION

It has been found that high surface area, in situ, pretreatable iron-cobalt slurry catalysts can be prepared by the process of adding an alpha-hydroxy aliphatic carboxylic acid, e.g., glycolic acid, to a basic aqueous solution containing dissolved iron and cobalt salts and subsequently evaporating the solution to dryness to yield an amorphous mixed metal oxide, which on calcining at elevated temperature, exhibits a spinel crystal structure and possesses a high surface area.

The unsupported high surface area Fe-Co spinels prepared in this manner, possess surface areas (BET) in the range of about 100–200 $m^2/g$ (square meters per gram), which are significantly higher than corresponding Fe-Co spinels prepared by a conventional process, e.g., 0.2–1.0 $m^2/g$.

After the addition of promoter agents, by surface deposition or impregnation, such as alkali carbonate, the high surface area spinels are then subjected to high temperature, e.g., 300°–400° C., $H_2$ reduction to obtain a fully reduced alloy, followed by treatment with $H_2/CO$ at 300°–400° C. to convert the alloy to a fully carburized state.

The resulting high surface are reduced and carburized catalysts, provide unusually high activity, selectivity and activity maintenance in the direct conversion of $CO/H_2$ to alpha-olefins under slurry reactor conditions. These catalysts are especially useful in low pressure slurry reactor systems where alpha-olefin residence times in the reaction zone can be minimized, and the physical properties of the catalyst bed are conducive to use of finely divided powdered catalysts.

In accordance with this invention, there is provided, a composition of matter comprising an unsupported, Group IA or IIA metal salt promoted iron-cobalt spinel or mixture thereof, said spinel exhibiting a single phase powder x-ray diffraction pattern substantially isostructural with $Fe_3O_4$, and possessing a BET surface area greater than 5 $m^2/g$ and an iron-cobalt atomic ratio of about 4 to 1 or above.

Further provided is a composition of matter comprising an iron-cobalt metallic alloy, being isostructural with metallic alpha-iron, as determined by X-ray diffractometry, and possessing a BET surface area greater than 5 $m^2/g$, said alloy being produced by contacting the above, described Fe:Co spinel with a reducing atmosphere.

Also provided is a composition of matter comprising a reduced and carbided iron-cobalt alloy, said composition being substantially isostructural with Chi-$Fe_5C_2$ (Hagg carbide), as determined by X-ray diffractometry, and possessing a BET surface area of greater than 5 $m^2/g$, said composition produced by contacting the above-described iron-cobalt alloy with a carbiding atmosphere. A related composition is also provided being isostructural with $Fe_3C$ (cementite) and having a BET surface greater than 5 $m_2/g$.

Furthermore, there is provided a process for producing the iron-cobalt spinel composition described above comprising the steps of: (a) evaporating a liquid solution comprising a mixture of iron and cobalt salts of at least one alpha-hydroxy aliphatic carboxylic acid, wherein the molar ratio of total moles of said acid to total moles of said iron and cobalt, taken as the free metals, is about 1:1 to above, and wherein the atomic ratio of iron:-cobalt, taken as the free metals in said mixture is greater than 2 to 1; yielding an amorphous residue; and (b) calcining said residue at elevated temperature for a time sufficient to yield an iron-cobalt spinel, exhibiting a single spinel phase, isostructural with $Fe_3O_4$, as determined by powder X-ray diffractometry.

In addition, there is provided a process for preparing the above-described iron-cobalt alloy composition of matter comprising contacting the above-described iron-cobalt spinel, with a reducing atmosphere under conditions of elevated temperature, pressure, space velocity for a time sufficient to substantially reduce the metal oxides of the spinel.

There is also provided a process for preparing the above-described reduced and carbided spinel comprising the step of contacting the above-described iron-cobalt metal alloy, with a carbiding atmosphere under conditions of elevated temperature, pressure, space velocity, for a time sufficient to substantially carbide said alloy.

There is further provided a process for synthesizing a hydrocarbon mixture containing $C_2$–$C_{20}$ olefins comprising the step of contacting a catalyst composition, comprised of an unsupported iron cobalt spinel, or mixture thereof, said spinel initially exhibiting a single spinel phase being isostructural with $Fe_3O_4$, as determined by X-ray diffractometry, and possessing an initial BET surface area greater than 5 $m^2/g$ and an Fe:Co atomic ratio of 4:1 or above, said contacting conducted with a mixture of CO and hydrogen under conditions of pressure, space velocity and elevated temperature for a time sufficient to produce said $C_2$–$C_{20}$ olefins.

DESCRIPTION OF THE INVENTION AND PREFERRED EMBODIMENTS

The subject high surface area iron-cobalt spinels are new compositions of matter which are isostructural with $Fe_3O_4$, as determined by X-ray diffractometry using copper K alpha radiation and exhibit a single spinel phase. By the term "spinel" is meant a crystal structure whose general stoichiometry corresponds to $AB_2O_4$, where A and B can be the same or different cations. Included within this definition is the commonly found spinel, $MgAl_2O_4$. A and B can have the following cationic charge combinations: $A=+2$, $B=+3$, $A=+4$, $B=+2$, or $A=+6$, $B=+1$. Spinels contain an approximately cubic close-packed arrangement of oxygen atoms with ⅛th of the available tetrahedral interstices and ½ of the octahedral interstices filled, and can exhibit hundreds of different phases. Further description of the spinel structure can be found in "Structural Inorganic Chemistry" by A. F. Wells, Third Edition, Oxford Press, and the Article "Crystal Chemistry and Some Magnetic Properties of Mixed Metal Oxides with the Spinel Structure" by G. Blasse, Phillips Research Review Supplement, Volume 3, pp 1–30, (1964). By the term "isostructural" is meant crystallizing in the same general structure type in that the arrangement of the atoms remains very similar with only minor changes in unit cell constants, bond energies, and angles. By the term "single spinel phase" is meant one structural and compositional formula, corresponding to a single spinel material into which all of the metal components are incorporated, and exhibiting one characteristic X-ray diffraction pattern.

The spinel possesses a BET surface area greater than 5 $m^2/g$ as determined by the well-known BET surface area measurement technique as described in reference JACS Vol. 60, p. 309 (1928) by S. Brunauer, P. H. Emmett, and G. Teller, and preferably the spinel has a surface area greater than 50 $m^2/g$ and particularly preferred of about 100 to 300 $m^2/g$. This obtained surface area is in contrast to conventional methods of spinel formation, e.g., high temperature sintering of component oxides in an oxygen-free atmosphere. The surface area is generally in the range of about 0.1 to 1 $m^2/g$. The high surface area obtained in the present process corresponds to about 0.01 to 0.002 microns in particle size.

The iron to cobalt atomic ratio of the metals in the spinel is 4:1 or above and is preferably in the range of 7:1 to 35:1, and particularly preferred in the range of 19–20:1.

The spinel can be represented by the formula: $Fe_xCo_yO_4$, wherein x and y are decimal or integer values other than zero, and wherein the sum of x plus y is 3 and the ratio of x to y is 4:1 and preferably being about 7 to 1 to 35 to 1. Particularly preferred is where the iron to cobalt atomic ratio is about 19 to 20 to 1.

Representative examples of the various spinels corresponding to the formula are $Fe_{2.85}Co_{0.15}O_4$, $Fe_{2.625}Co_{0.375}O_4$, $Fe_{2.97}Co_{0.03}O_4$ and $Fe_{2.25}Co_{0.75}O_4$. The composition utilized may comprise a mixture of spinels in which at least two iron-cobalt spinels are present, being isostructural with $Fe_3O_4$, having BET surface areas greater than 5 $m^2/g$, wherein said spinels individually possess different iron-cobalt atomic ratios, being 4:1 or above.

Physical properties, in general, of these subject spinels are similar to those of magnetite, $Fe_3O_4$, and include: melting point above 1400° and brown to black in color.

The iron-cobalt spinels are generally used in unsupported form in the slurry process.

A promoter agent can also be used in the composition and can be used to particularly promote olefin formation, for example, in the process. General classes of suitable promoter agents include hydroxides carbonates, bicarbonates, organic acid salts, e.g. acetates, inorganic acid salts, e.g., nitrates, halides, sulfates, of Group IA and IIA metals including lithium, sodium, potassium, rubidium, cesium, barium, calcium, strontium, magnesium, and the like. These promoters can be added to the iron-cobalt spinel, if desired, simply by impregnating the iron-cobalt spinel composition with an aqueous solution of one or more of said promoter agents and drying the resulting impregnate.

Representative examples of specific promoter agents are potassium carbonate, potassium sulfate, potassium bicarbonate, cesium chloride, rubidium nitrate, lithium acetate, potassium hydroxide, and the like. Preferred are the Group IA compounds and a particularly preferred promoter agent is potassium carbonate.

The promoter, if used, is generally present in about a 0.1 to 10 gram-atom % of metal ion based on the total combined metals gram-atoms. A preferred level of promoter agent is in the range of 1 to 2 gram-atom %. A particularly preferred spinel composition of the subject invention is $Fe_{2.85}Co_{0.15}O_4$/1 % K as potassium carbonate. In the empirical formulas used herein, the amount of the promoter agent, e.g., potassium, is expressed in terms of gram atom percent based on the total gram-atoms of metals used. Thus, "1 gram-atom percent of potassium" signifies the presence of 1 gram-atom of potassium per 100 total gram atoms of combined gram atoms of Fe and Co.

The utility of the subject spinels is their ability, to undergo unexpectedly facile in situ reduction in the slurry liquid and pretreatment to form iron-cobalt alloys, which are further in situ carbided to form active slurry catalysts in a Fischer-Tropsch slurry process for making $C_2$–$C_{20}$ olefins from CO/hydrogen.

The subject spinel composition can be made by a process in which a basic aqueous solution of cobalt and iron salts of an alpha-hydroxy aliphatic carboxylic acid, is evaporated to dryness, leaving an amorphous residue, which is then heated at elevated temperature to substantially form the spinel, in a single spinel phase, being isostructural with $Fe_3O_4$ and possessing a surface area greater than 5 m/g, preferably above 50 $m^2/g$. The heating is conducted such that no significant loss in surface area of the final spinel is incurred.

The key to the synthesis of the subject spinels is in the use of an organic, saturated, aliphatic, alpha-hydroxy carboxylic acid to form a complex salt, which is soluble in the aforementioned aqueous medium, at a pH on the acidic side, i.e. pH of 5–7. The solubility of the iron and cobalt organic salts of the alpha-hydroxy carboxylic acid prevent crystallization from occurring, resulting in a crystalline product being obtained from the solution, which would possess a relatively low surface area.

The subject method utilizes an alpha-hydroxy aliphatic carboxylic acid which acts as a solubilizing agent for the iron and cobalt salts in the aqueous solution. Any saturated aliphatic alpha-hydroxy carboxylic acid, containing at least one alpha-hydroxy grouping, can be used to form the soluble iron and cobalt salts in the subject invention process in mildly basic aqueous solution, is deemed to be included within the scope of this invention. Representative examples of such acids which can be mono-hydroxy or di-hydroxy or mono-carboxylic or di-carboxylic are glycolic, malic, glyceric, mandelic, tartaric, lactic acids and mixtures thereof. A preferred carboxylic acid used in the process is glycolic acid.

The amount of acid used is at least the stoichiometric amount, i.e., 1 to 1 molar ratio for each metal present and preferably in about a 5–10% molar excess of the stoichiometric amount. Higher ratios can be used, if it is economical to do so. Lower amounts can also be used but would result in incomplete iron and cobalt acid salt formation.

The first step in the process comprises forming an aqueous solution by dissolving iron salts and cobalt salts, in a water-soluble salt form such as their nitrates, sulfates, chlorides, acetates, and the like, in water.

The concentration of the salts in the aqueous liquid is not critical to the extent that the salts are present in less than a saturated solution to avoid precipitation. For example, an 80–90% saturated solution, of combined dissolved metal molarities for avoiding precipitation in the process, can be effectively used.

The temperature of the aqueous solution is not critical and may be above room temperature to aid in the solubilizing process. However, room temperature is adequate and is the temperature generally used in the process. The pressure also is not critical in the process and atmospheric pressure is generally used.

The aqueous solution can also contain a small amount of organic solvent such as ethanol, acetone, and the like for aiding in the solubilizing of the iron and cobalt salts of the alpha-hydroxy carboxylic acid.

Following the dissolving of the iron and cobalt salts, the alpha-hydroxy carboxylic acid is added, together with a sufficient quantity of base, usually being ammonium hydroxide, sodium hydroxide, potassium hydroxide, and the like, preferably ammonium hydroxide, to solubilize the resulting acid salts. The amount of base added is sufficient to keep the pH in the range of about 5 to 7.0.

It should be noted that the exact sequence of steps need not be adhered to as described above, with the proviso that the resulting aqueous solution contain dissolved iron and cobalt salts in stoichiometric amounts as iron and cobalt salts of alpha-hydroxy carboxylic acid in solution. If there are any insoluble materials present after addition of the base and organic acid, they should be filtered prior to the evaporation step.

At this point, the resulting solution is evaporated, as for example, by air drying, or under reduced pressure, at elevated temperature, as practiced in a rotary evaporator, or in a vacuum drying oven.

The resulting material from the evaporation step is an amorphous residue, generally being a powder. This residue is heated at elevated temperature at 100° to 600° C. for about 1 to 24 hours in generally air to result in a substantially single spinel phase which is isostructural with $Fe_3O_4$, as determined by X-ray diffractometry, as previously described herein. Preferred temperature range is 100°–400° C., and particularly preferred is about 350° C. for single phase spinel formation.

A further subject of the instant invention is a composition of matter being a reduced iron-cobalt metallic alloy formed from the spinel described above, said alloy being isostructural with alpha-iron, as determined by X-ray diffractometry, and preferably possessing a BET surface area of about 5 to 10 $m^2/g$ and above or higher.

Generally preferred is where the surface area is about 5–10 $m^2/g$ and particularly preferred being 6–8 $m^2/g$. The atomic ratio of iron to cobalt is not restricted and can be 4:1 and above. Generally, however, for $C_2$–$C_{20}$ olefin synthesis in the subject process described herein, the iron-cobalt atomic ratio is preferably about 4 to 1 and above and more preferably being about 7 to 1 to 35 to 1 and a particularly preferred range is of about 19–20:1.

The iron-cobalt alloy can be produced by reducing the above-described iron-cobalt spinel in a reducing atmosphere at elevated temperature generally of about 240° C. and above and preferably 300° to 400° C. The reduction can be carried out with various reducing gases including hydrogen, $H_2/CO$, and the like, and mixtures thereof. Preferably hydrogen gas alone is generally used in an inert carrier medium such as helium, neon, argon, or nitrogen, in the absence of CO when substantially pure, non-carbided alloy is desired.

The alloy can be prepared ex situ in a tube reactor or in situ in the Fischer-Tropsch slurry process. The in situ preparation is conducted in the slurry apparatus when the above described spinel is reduced while suspended in the slurry liquid, in a reducing atmosphere being preferably a hydrogen atmosphere at elevated temperature being about 240° C., or above, preferably at 240°–300° C., at a space velocity, pressure, and hydrogen concentration sufficient to cause substantial reduction of the spinel to the alloy. Substantial reduction is complete when the X-ray diffraction pattern shows a pattern substantially isostructural with alpha-iron.

The above-described alloy is useful in forming a carbided iron-cobalt catalyst useful in the subject Fischer-Tropsch slurry process for making $C_2$–$C_{20}$ olefins, as described herein.

Also, subjects of the instant invention are compositions of matter being reduced and carbided iron-cobalt alloys, one being isostructural with $Fe_5C_2$, "Hagg carbide" as described in *Trans. of the Iron & Steel Inst. of*

Japan, Vol. 8, p. 265 (1968) by Nagakura et al., as determined by X-ray diffractometry and possessing a BET surface area of greater than 5 m$^2$/g; and two, being isostructural with Fe$_3$C "cementite", as determined by X-ray diffractometry, and possessing a BET surface area of greater than 5 m$^2$/g.

Preferred is where the surface area of either material is about 25–200 m$^2$/g and particularly being preferred of about 60–150 m$^2$/g, including both the formed Fe-Co carbide and surface carbon formed during the carbiding step.

The atomic ratio of the iron:cobalt is not restricted for either composition but generally for use in the subject process for producing C$_2$–C$_{20}$ olefins is 4:1 or above and preferably 7:1 to 35:1 and particularly preferred in the range of about 19–20:1.

The carbided iron-cobalt alloy, having an X-ray diffraction pattern isostructural with Fe$_5$C$_2$, can be produced by carbiding the iron-cobalt alloy, described hereinabove, in a suitable carbiding atmosphere at elevated temperature of up to about 400° C. Temperatures above 500° lead to formation of Fe-Co carbides which are isostructural with Fe$_3$C, cementite.

Carbiding atmospheres which can be used to produce the subject reduced, carbided, catalyst include CO, CO/hydrogen, aliphatic hydrocarbons, aromatic hydrocarbons, and the like. A preferred carbiding atmosphere is CO/hydrogen. When using CO/hydrogen carbiding atmosphere, mixtures of CO/hydrogen can be used in a 1:10 to 10:1 molar ratio. A preferred ratio used for carbiding purposes is a 1:1 molar ratio.

The carbiding step is generally conducted at a temperature of about 250° C., or above and preferably at 300° to 400° C. A preferred method of carbiding the alloy is in situ in the slurry liquid to be used in the Fischer-Tropsch process. A particularly preferred method is where the spinel is treated with a mixture of CO/hydrogen and reduced and carbided in situ in one step prior to hydrocarbon synthesis. The pressure is generally about 1 atmosphere, and a space velocity of about 20–20,000 v/v/hr is chosen in order to completely carbide the starting iron-cobalt oxide which can be determined by X-ray diffractometry when the material becomes isostructural with Haag carbide, Fe$_5$C$_2$. The Haag-type Fe-Co carbides produced in this process are of the general formula: Fe$_{5-(5/3)y}$Co$_{(5/3)y}$C$_2$, and also include surface carbon produced during the carbiding process. Carbiding temperatures above 500° C. and preferably 500°–700° C., lead to formation of a mixed Fe-Co carbide of the general formula Fe$_{3-y}$Co$_y$C, which is generally formed under ex situ procedures which allow the use of higher temperatures than possible in the in situ slurry process.

The resulting carbide is an active slurry catalyst for producing C$_2$–C$_{20}$ olefins in the described Fischer-Tropsch slurry process.

Also, the above-described alloy and carbide, can be prepared independently of the slurry apparatus and may be pyrophoric and inconvenient to handle. In that case, the material may be passivated by contact with oxygen for a sufficient time to reduce or eliminate the pyrophoric tendency. Generally, the oxygen used in the passivating process is used in an inert gas stream carrier such as helium for a sufficient time to cause passivation. Generally, this is conducted preferably at room temperature, at a pressure and space velocity which are convenient and easy to control and to maximize the efficiency of the process needed for complete passivation.

Also, a subject of the instant invention is a Fischer-Tropsch process for producing C$_2$–C$_{20}$ olefins by utilizing the iron-cobalt spinel, iron-cobalt alloy and the reduced, carbided, iron-cobalt spinel catalyst described hereinabove.

Although a fixed bed process can be used, a preferred process mode for operating the Fischer-Tropsch process utilizing the catalysts described herein is a slurry-type process wherein the catalyst in fine particle size and high surface area being above 5 m$^2$/g is suspended in a liquid hydrocarbon and the CO/hydrogen mixture forced through the catalyst slurry allowing good contact between the CO/hydrogen and the catalyst to initiate and maintain the hydrocarbon synthesis process.

Advantages of a slurry process over that of a fixed bed process are that there is better control of the exothermic heat produced in the Fischer-Tropsch process during the reaction and that better control over catalyst activity maintainance by allowing continuous recycle, recovery, and rejuvenation procedures to be implemented. The slurry process can be operated in a batch or in a continuous cycle, and in the continuous cycle, the entire slurry can be circulated in the system allowing for better control of the primary products residence time in the reaction zone.

The subject process can use any of the above-described materials, as catalyst or catalyst precursors: the iron-cobalt spinel isostructural with Fe$_3$O$_4$; the iron-cobalt alloy isostructural with alpha-iron; or, the reduced, carbided, iron-cobalt alloy which is isostructural with Fe$_5$C$_2$, or Fe$_3$C. All the materials must have a BET surface area of greater than 5 m$^2$/g, to be applicable in the efficient claimed slurry process described herein. These materials can also be made independently of the apparatus prior to use or can be made in situ in the apparatus during the carrying out of the process. A preferred procedure is where the spinel, in high surface area form is pretreated in situ in the slurry liquid, in either distinct reduction-carbiding steps or in one reduction-carbiding step as with CO/hydrogen at elevated temperature. A full discussion of each of the materials, their properties and their preparation are given hereinabove and need not be reiterated.

The slurry liquid used in the process is a liquid at the reaction temperature, must be chemically inert under the reaction conditions and must be a relatively good solvent for CO/hydrogen and possess good slurrying and dispersing properties for the finely divided catalyst. Representative classes of organic liquids which can be utilized are high boiling paraffins, aromatic hydrocarbons, ethers, amines, or mixtures thereof. The high boiling paraffins include C$_{10}$–C$_{50}$ linear or branched paraffinic hydrocarbons; the aromatic hydrocarbons include C$_2$–C$_{20}$ single ring and multi- and fused ring aromatic hydrocarbons; the ethers include aromatic ethers and substituted aromatic ethers where the ether oxygen is sterically hindered from being hydrogenated; the amines include long chain amines which can be primary, secondary, and tertiary amines, wherein primary amines preferably contain at least a C$_{12}$ alkyl group in length, secondary amines preferably contain at least two alkyl groups being C$_7$ or greater in length, and tertiary amines preferably contain at least three alkyl groups being C$_6$ or higher in length. The slurry liquid can contain N and O in the molecular structure but not S, P, As or Sb, since these are poisons in the slurry process. Representative examples of specific liquid slurry solvents useful are dodecane, tetradecane, hexadecane, octadecane, cosane, tetracosane, octacosane, dotriacontane, hexatriacontane, tetracontane, tetratetracontane, toluene, o-, m-, and p-xylene, mesitylene, $C_1$-$C_{12}$ mono- and multi-alkyl substituted benzenes, dodecylbenzene, naphthalene, anthracene, biphenyl, diphenylether, dodecylamine, dinonylamine, trioctylamine, and the like. Preferred liquid hydrocarbon slurry solvent is octacosane or hexadecane.

The amount of catalyst used in the liquid hydrocarbon slurry solvent is generally about 10 to 60 g. of dry catalyst per 500 g. slurry liquid. Preferably about 30 to 50 g. dry catalyst per 500 g. slurry liquid slurry is utilized, being in about a respective 5:1 to 10:1 weight ratio.

The slurry system, comprised of the slurry liquid and finally divided catalyst, is generally stirred to promote good dispersion during the pretreatment in the process to avoid catalyst settling and to eliminate mass transport limitations between the gas and liquid phases. In a typical laboratory unit the rate of stirring is generally carried out in the range of about 600 to 1,200 rpm and preferably 1,000 to 1,200 rpm.

Prior to the CO/hydrogen hydrocarbon synthesis run, the reduced and carbided iron-cobalt catalyst is generally conditioned in the apparatus by purging with nitrogen to remove reactive oxygen-containing gases and then the temperature is increased while stirring to the reaction temperature range. Then the system is generally subjected to a hydrogen treatment for a sufficient time to insure complete removal of any surface metal oxide present which would interfere in hydrocarbon synthesis.

Optionally, and preferably if the catalyst is prepared in situ, then the hydrogen treatment is generally not required or is only practiced for a short period of time. The pressure and space velocity during the inert gas-hydrogen conditioning step are not critical and can utilized in the range which is actually used during actual hydrocarbon synthesis.

Following the conditioning step, the CO/hydrogen feedstream is introduced into the slurry catalyst chamber and the pressure, space velocity, temperature, and hydrogen/CO molar ratio is then adjusted, as desired, for hydrocarbon synthesis conditions.

In the process, the hydrogen and CO are used in a molar ratio in the gaseous feedstream in about a 10:1 to 1:10 molar ratio, preferably 3:1 to 0.5:1, and particularly preferred 1:1 to 2:1 molar ratio.

The temperature in the process is generally in the range of about 200° to 300° C., preferably being 230° to 270° C., and particularly preferred of about 240°-260° C. Higher temperature ranges can also be used but tend to lead to lighter products and more methane, lower temperature ranges can also be used but tend to lead to lower activity and wax formation.

The pressure useful in the process is generally conducted in the range of about 50 to 400 psig and preferably about 70 to 225 psig. Higher pressures can also be used but tend to lead to waxy materials particularly in combination with lower temperature.

The space velocity used in the process is generally about 100 to 4,000 volumes of gaseous feedstream/per volume of dry catalyst in the slurry/per hour and is preferably in the range of about 400 to 1,200 v/v/hr, and particularly preferred of 800-1,200 v/v/hr. Higher space velocities can also be used but tend to lead to lower % CO conversion, and lower space velocities can also be used but tend to lead to more paraffinic products.

Generally, after the pretreatment, the CO/hydrogen feedstream is introduced to initiate and maintain hydrocarbon synthesis. By the use of the above-described catalysts in the system, the activity maintenance is very good and on a laboratory scale, e.g., 500 cc of slurry containing 50 g of catalyst described herein, 30 days of continuous run have been observed without significant decline in percent CO conversion activity while maintaining good $C_2$-$C_{20}$ olefin synthesis activity.

The percent CO conversion obtainable in the subject process, while providing substantial quantities of $C_2$-$C_{20}$ olefins, ranges from about 30 to 80 percent and usually about 50 to 60 percent for sufficient $C_2$-$C_{20}$ olefin production.

"Total hydrocarbons" produced in the process is related to the selectivity of percent CO conversion to hydrocarbons being those hydrocarbons from $C_1$ to about $C_{40}$ inclusive. Total hydrocarbon selectivity is generally 0 to 50 percent and higher, of the total CO converted, and the remainder converted to $CO_2$.

The percent $C_2$-$C_{20}$ hydrocarbons of the total hydrocarbons produced including methane and above is about 60 to 90 wt. %. The percent of $C_2$-$C_{20}$ olefins produced, of the $C_2$-$C_{20}$ total hydrocarbons produced is about 60 to 70 wt. %. The olefins produced in the process are substantially alpha olefins.

The selectivity to methane based on the amount of CO conversion is about 1 to 10 weight percent of total hydrocarbons, produced. Preferably about 5 percent, and lower, methane is produced in the process.

As discussed above, the percent selectivity to $CO_2$ formation in the process is about 10 to 50 percent of CO converted.

Preferably, the reaction process variables are adjusted to minimize $CO_2$ production, minimize methane production, maximize percent CO conversion, and maximize percent $C_2$-$C_{20}$ olefin selectivity, while achieving activity maintenance in the catalyst system.

Generally, this format can be derived in a preferred mode of operating the process where the slurry liquid used is hexadecane, the catalyst used is $Fe_{2.85}Co_{0.15}O_4$/1% K as $K_2CO_3$, the catalyst/liquid weight ratio is 40/500, the system is stirred at 1,200 rpm, and pretreatment procedure is conducted in situ in a one step procedure using 9:1 $H_2/N_2$ at 220° C., atmospheric pressure, 1200 v/v/hr. space velocity, for a period of 5 hrs., and the process conducted at the hydrogen:CO molar ratio is 1:1, the temperature is conducted at about 245° C., at a pressure of 7-150 psig, and space velocity 1,000-1200 v/v/hr. By carrying out the above process in the stated variable ranges efficient activity maintenance and production of $C_2$-$C_{20}$ olefins can be achieved.

The effluent gases in the process exiting from the reactor may be recycled if desired to the reactor for further CO hydrocarbon synthesis.

Methods for collecting the products in the process are known in the art and include fractional distillation, and the like. Methods for analyzing the product liquid hydrocarbons and gaseous streams are also known in the art and generally include gas chromatography, liquid chromatography, high pressure liquid chromatography and the like.

Apparatus useful in the preferred process is any conventional slurry-type reactor, being horizontal or vertical, being stationary or cyclical, in catalyst slurry.

11

Other apparatus not specifically described herein will be obvious to one skilled in the art from a reading of this disclosure.

EXAMPLES

The following Examples are illustrative of the best mode of carrying out the invention as contemplated by us and should not be construed as being limitations on the scope and spirit of the instant invention.

Unless otherwise indicated, the selectivity weight percentages of product hydrocarbons is given on a $CO_2$-free basis.

It should be further noted that the data in Example 8 was obtained utilizing a large scale slurry apparatus and the data was analyzed for alcohols content as reported. The previous examples did not analyze for or report an alcohols content and it is reasonably believed to be below 15% of total products in the small scale apparatus.

EXAMPLE 1

Preparation of $Fe_{2.85}Co_{0.15}O_4$ Spinel 198.04 grams of ferric nitrate in 144 cc of water and 7.5 grams of cobalt nitrate in 8 cc of water were mixed together. To this solution was added a solution of 41.6 grams of 85% glycolic acid containing 45 cc of ammonium hydroxide such that the resulting pH of the ammonium glycolate solution was about 6.5. The ammonium glycolate solution constituted 0.51 moles of glycolic acid such that about a one to one molar ratio of total metals including iron and cobalt to glycolic acid resulted. The ammonium glycolate solution was added to the aqueous solution containing iron and cobalt salts and the contents stirred. The resulting solution was allowed to evaporate by air drying. Upon drying at room temperature the resulting solid was shown by X-ray diffraction to be an amorphous material because of lack of sharp discrete reflections. The solid was heated in air at 350° C. for 2 hours. An X-ray diffraction pattern of the resulting material showed it to be a single phase cobalt-iron spinel isomorphous with $Fe_3O_4$. The X-ray diffraction peaks were broadened relative to a compositionally equivalent material obtained by a high temperature procedure. This indicated that the resulting obtained material was of very small particle size. The surface area of the resulting material was about 200 square meters per gram. Carbon analysis of the material indicated approximately 0.15% carbon percent. The resulting material was impregnated with one gram atomic percent of potassium using an aqueous solution of potassium carbonate and drying of the resulting impregnated sample at 125° C. The resulting solid had an empirical formula of $Fe_{2.85}Co_{0.15}O_4$/1% K.

Preparation of Alloy

The above obtained oxide was reduced at 400° C. in a stream of 15 volume percent hydrogen/85% helium at 200 v/v/hr (SHSV) for 4 hours. One percent of oxygen in helium was introduced at room temperature for one hour to passivate the material. The X-ray of the resulting material was isostructural with alpha iron. The resulting BET nitrogen surface area was 8 m$^2$/g.

Preparation of Carbide

The above reduced material was treated at 400° C. in a stream of 15 volume percent hydrogen/80% helium/5% CO at 200 v/v/hr. for four hours. Following this the sample was cooled to room temperature and 10% oxygen in helium was introduced for one hour to passivate the material. The X-ray diffraction pattern of the resulting material was isostructural with $Fe_5C_2$. The BET nitrogen surface area of the material was about 118 m$^2$/g. Analysis showed that about 60–70 weight percent of the material was carbon and thus the material was a composite of $Fe_{4.75}Co_{0.25}C_2$/1 gram-atom % K and surface carbon.

EXAMPLE 2

Into a slurry reactor, being a 300 cc Parr CSTR (continuous stirred tank reactor) was charged: 50 g of octacosane and 5.0 of the high surface area spinel, described above in Example 1. The system was purged with nitrogen and then $H_2$ while the temperature was increased from room temperature to 220° C., where the system was maintained under these conditions in a hydrogen atmosphere with stirring for a one-hr period at 600 rpm. The system was then placed under CO hydrogenation reaction conditions by adjusting the reaction temperature to 270° C., the $H_2$/CO volume ratio to 1:1, the space velocity to 1200 V gaseous feedstream/V dry catalyst/hr, the pressure to 70 psig, and the slurry stirrer speed to 600 rpm in the octacosane solvent. The effluent gas from the reactor was monitored by an HP-5840A Refinery Gas Analyzer to determine percent CO conversion and the nature of the hydrocarbon products. The results are listed below in Table I under the high surface area spinels as "oxide".

Further runs were made based on the spinel which was (1) reduced ex situ, and (2) reduced/carbided ex situ, prior to being charged into the slurry liquid. The results are listed below in the Table as "reduced" and "reduced/carburized", respectively, together with the specific pretreatment conditions. The control, and the low surface area spinel also run under substantially the same conditions, are listed below.

The listed comparative sample, $Fe_2O_3$, was obtained from Alpha Chemicals and had a BET surface area of less than 10 m$^2$/g.

The listed comparative sample $Fe_{2.85}Co_{0.15}O_4$/1% K was made by sintering an intimate mixture of $Fe_2O_3$, Fe metal and $Co_3O_4$, in the appropriate molar ratio, at 800°–1,000° C. for 24 hours in an evacuated sealed tube. The solid was collected, crushed, pelletized and then the sintering procedure repeated. The obtained solid was crushed and then impregnated with aqueous potassium carbonate and then dried at 125° C. for several hours in a drying oven. The surface area of the obtained solid was about 0.3 m$^2$/g.

TABLE I

Slurried F-T Catalysts with 1:1 $H_2$:CO

| Catalysts | % CO Conv. | % $CO_2$ | % $CH_4$ | % $C_2$–$C_4$ | % Olefin $C_2$–$C_4$ |
|---|---|---|---|---|---|
| $Fe_2O_3$ | <4.0 | — | — | — | — |
| $Fe_{2.85}Co_{.15}O_4$/ 1% K | <4.0 | — | — | — | — |
| Spinels (100 + m$^2$/g) $Fe_{2.85}Co_{0.15}O_4$ | | | | | |
| Oxide | 78 | 48 | 3.1 | 7.3 | 92 |
| Reduced[a] | 55 | 62 | 2.2 | 10.9 | 88 |
| Reduced/Carburized[b] | 79 | 48 | 4.5 | 16.0 | 92 |

Conditions: 270° C., 1:1 $H_2$:CO, 1200 v/v/cat/hr. 70 psig, 600 rpm, octacosane solvent.
[a] $H_2$ at 350° C. for 12 hours and 400° C. for 24 hours.
[b] $H_2$/CO at 350° C. for 12 hours and 400° C. for 24 hours.

As is seen in this example, catalysts prepared from the high surface area spinel gave higher activity and $C_2$–$C_4$ olefin selectivity than conventional iron oxide catalysts.

EXAMPLE 3

The catalysts, apparatus, catalyst pretreatment and general CO hydrogenation procedures of Example 2 were used and repeated except that modified CO hydrogenation conditions were used at 250° C. and 2:1 $H_2$:CO as listed in Table II.

TABLE II

Slurried F-T Catalysts with 2:1 $H_2$:CO

| Catalysts | % CO Conv. | % $CO_2$ | % $CH_4$ | % $C_2$–$C_4$ | % Olefin $C_2$–$C_4$ |
|---|---|---|---|---|---|
| $Fe_2O_3$ | <5.0 | 20+ | 15+ | 14.0 | 60.0 |
| *$Fe_{2.85}Co_{.15}O_4$/1% K | <4.0* | NA | NA | NA | NA |
| Spinels (100 + $m^2$/g) $Fe_{2.85}Co_{0.15}O_4$ | | | | | |
| Oxide | 31 | 62 | 4.1 | 18.2 | 90 |
| Reduced[a] | 54 | 63 | 2.4 | 11.1 | 89 |
| Reduced/Carburized[b] | 64 | 50 | 3.6 | 14.0 | 83 |

Condition: 250° C., 2:1 $H_2$:CO, 1200 v/v/cat/hr. 70 psig, 600 rpm, octacosane solvent.
*Note:
less than 5% conversion observed even at 270° C.
[a]$H_2$ at 350° C. for 12 hours and 400° C. for 24 hours.
[b]$H_2$/CO at 350° C. for 12 hours and 400° C. for 24 hours.

EXAMPLE 4

Utilizing the catalysts, apparatus, catalyst pretreatment and general CO/hydrogenation procedures described in Example 2, the following runs were made utilizing the specific process conditions listed in Table III below:

TABLE III

Comparative Study of Fe—Co Catalysts from High and Low Surface Spinel Precursors

| Spinel Initial Surface Area | $Fe_{2.85}Co_{.15}O_4$/1% K | |
|---|---|---|
| | 100 + $m^2$/g | <10 $m^2$/g |
| % CO Conversion | 45 | 44 |
| % CO to $CO_2$ | — | — |
| % CO to HC | — | — |
| Wt % Selectivity | | |
| $CH_4$ | 1.9 | 2.0 |
| $C_2$–$C_4$ | 8.3 | 8.4 |
| $C_5$+ | 32.3 | 23.6 |
| $CO_2$ | 57.0 | 66.0 |
| % Olefin in $C_2$–$C_4$ | 90 | 90 |

Conditions:
250° C., 1200 v/g CAT/hr, 1:1 $H_2$:CO, 70 psig, 600 RPM, octacosane solvent. Catalysts subjected to ex situ $H_2$ treatment at 300+° C. followed by ex situ $H_2$/CO treatment 350+° C. to affect complete reduction-carburization followed by oxygen passivation.

The results in Table III indicate that catalysts prepared from low and high surface area Fe-Co spinels provide comparable performance when they are both fully prereduced and carburized ex situ. The catalyst derived from the low surface area precursor generated more $CO_2$ and less $C_5$+ hydrocarbon than the catalyst generated from the high surface area precursor, under the stated reaction conditions.

EXAMPLE 5

Utilizing the catalysts, apparatus, pretreatment and general CO hydrogenation procedures described in Example 2, the following runs were made under the specific process conditions listed below in Table IV:

TABLE IV

Comparative Study of Carburized Catalysts from High Surface Area Spinel Precursors

| Catalyst Precursor | A[a] | B[b] | $Fe_3O_4$/1% K[c] |
|---|---|---|---|
| % CO Conversion | 64 | 42 | 65 |
| % CO to $CO_2$ | 36 | 24 | 39 |
| % CO to HC | 28 | 18 | 26 |
| Wt. % Selectivity | | | |
| $CH_4$ | 3.6 | 4.1 | 5.1 |
| $C_2$= | 4.2 | 2.8 | 2.6 |
| $C_2$° | 0.6 | 1.1 | 1.6 |
| $C_3$= | 5.1 | 6.0 | 6.7 |
| $C_3$° | 0.6 | 0.7 | 0.8 |
| $C_4$= | 2.7 | 3.1 | 3.6 |
| $C_4$° | 0.4 | 0.6 | 0.8 |
| $C_5$+ | 26.6 | 25.6 | 18.8 |
| $CO_2$ | 56 | 56 | 60 |
| % Olefin in $C_2$–$C_4$ | 88 | 83 | 80 |

[a]$Fe_{2.85}Co_{0.15}O_4$/1% K @ 100 + $m^2$/g.
[b]same as A but less than 1 $m^2$/g.
[c]surface area = 100 + $m^2$/g.
Conditions:
250° C., 1200 V/G CAT/hr, 2:1 $H_2$:CO, 70 psig, 600 RPM, octacosane, ex situ treated in $H_2$ at 300°+ C. and then $H_2$/CO at 350° C.+.

As seen, catalysts generated from Fe-Co and Fe spinel precursors which are fully reduced and carbided ex situ, exhibited comparable activity under CO hydrogenation conditions. However, the Fe-Co based system generated less unwanted $CH_4$ and $CO_2$ and a $C_2$–$C_4$ fraction which is richer in alpha-olefins when compared to the Fe only analog.

Comparison of Fe-Co catalysts from high and low surface area spinel precursors, Runs A and B, indicates that the high surface precursor generated higher yields of alpha-olefins and lower methane than the low surface area precursor when both catalysts are prereduced/carbided ex situ. Similar results were noted in previous Example 4.

EXAMPLE 6

Utilizing the spinel catalysts, apparatus, and general CO hydrogenation conditions described in Example 2, the following runs were carried out utilizing the specific in situ pretreatment and hydrocarbon synthesis process conditions listed below in Table V:

TABLE V

Comparative Study of High Surface Area Oxide Catalysts

| Catalyst Surface Area | $Fe_{2.85}Co_{.15}O_4$/1% K 100 + $m^2$/g | $Fe_3O_4$/1% K 100 + $m^2$/g |
|---|---|---|
| % CO Conversion | 60 | 8 |
| % CO to $CO_2$ | 36 | 5.2 |
| % CO to HC | 24 | 2.8 |
| Wt % Selectivity | | |
| $CH_4$ | 1.8 | 4.0 |
| $C_2$–$C_4$ | 8.0 | 15 |
| $C_5$+ | 30.2 | 11 |
| $CO_2$ | 60.0 | 65 |
| % Olefin in $C_2$–$C_4$ | 88 | 80 |

Conditions:
250° C., 1200 V/G CAT/hr, 2:1 $H_2$:CO, 70 psig, 600 RPM octacosane. Catalyst charged to reactor as oxide, treated in situ with $H_2$ at 100 psig at 200° C. for 1 hr before use.

As is seen, catalysts derived from high surface area spinels, with and without added cobalt, exhibited substantially different activities when employed and pretreated in situ directly under slurry reactor conditions. The Fe-Co catalyst is ca. 5-fold more active than the Fe only catalyst. The Fe-Co catalyst also generated less CH$_4$ and CO$_2$ than the Fe only catalyst and generates a C$_2$–C$_4$ fraction which is richer in alpha-olefins.

EXAMPLE 7

Utilizing the catalysts, apparatus, pretreatment and general CO hydrogenation procedures described in Example 2, the following runs were made using the specific conditions listed below in Table VI including comparative runs made at H$_2$/CO ratios of 1.0 and 2.0.

TABLE VI

| | Performance of Fe and Fe—Co Alloy Catalysts | | | |
|---|---|---|---|---|
| Precursor | Fe$_3$O$_4$/1% K[a] | | Fe$_{2.85}$Co$_{.15}$O$_4$/1% K[b] | |
| % CO Con. | 44 | 28 | 55 | 54 |
| H$_2$/CO | 1.0 | 2.0 | 1.0 | 2.0 |
| % CO to CO$_2$ | 26 | 15 | 34 | 34 |
| % CO to HC | 18 | 13 | 21 | 20 |
| Wt. % Sel. | | | | |
| CH$_4$ | 1.8 | 1.0 | 2.2 | 2.4 |
| C$_2$–C$_4$ | 11.1 | 5.0 | 10.9 | 11.1 |
| C$_5$+ | 28.1 | 41.0 | 24.8 | 23.5 |
| CO$_2$ | 59 | 53 | 62 | 63 |
| % Olefin in C$_2$–C$_4$ | 93 | 94 | 88 | 91 |

Conditions:
270° C., 1:1 H$_2$:CO, 1200 v/v Cat./hr., 70 psig, 600 rpm. Catalyst prereduced ex situ in H$_2$ at 350° C. for 12 hours and 400° C. for 24 hours.
[a]Initial spinel surface area - about 100 m$^2$/g.
[b]Initial spinel surface area - about 100 m$^2$/g.

EXAMPLE 8

Utilizing the pretreatment and general CO hydrogenation procedures described in Example 2, the following runs were made utilizing the specific catalyst and CO hydrogenation conditions described below.

The spinel described in Example 2, Fe$_{2.85}$Co$_{0.15}$O$_4$/1% K, was reduced and carbided ex situ similar to the procedure described i Example 2. A hydrogen/CO/helium feedstream in 1:1:7 molar ratio at 350+ C. and about 300 v/v/hr. for 24 hours was used. Powder X-ray diffraction analysis revealed the resulting material was isostructural with Hagg Carbide, Fe$_5$C$_2$. The elemental analysis of the material showed it to contain: Fe and Co in about a 19:1 atomic ratio and about 60–70 weight percent carbon. The surface area of the material was determined to be about 180–200 m$^2$/g.

The catalyst (40 cc. catalyst volume) was run under two different pressures in CO hydrogenation under the conditions listed below in Table VII.

The apparatus used was a 1 liter stirred tank reactor (316 S.S.) equipped with a Magnedrive TM head and an internal gas recycle.

TABLE VII

| | Fe$_{4.75}$CO$_{.25}$C$_2$/1% K | |
|---|---|---|
| % CO Conversion | 24 | 53 |
| % CO to CO$_2$ | 11 | 23 |
| % CO to HC | 13 | 30 |
| Pressure (psig) | 75 | 150 |
| Wt. % Selectivity | | |
| CH$_4$ | 4.9 | 4.7 |
| C$_2$=—C$_{20}$= | 59.3 | 53.2 |
| C$_1$–C$_{10}$ Alcohols | 7.8 | 11.5 |
| C$_{20}$°–C$_{20}$° | 26.2 | 20.6 |
| C$_{21}$+ | trace | 10.6 |

Conditions:
240° C., 1:1 H$_2$/CO, 1,000 v/v/hr. 1,200 RPM, 100–150 hr. on stream.

What is claimed is:

1. A composition of matter comprising an unsupported, Group IA or IIA metal salt promoted iron-cobalt spinel, or mixture thereof, said spinel exhibiting a single phase powder X-ray diffraction pattern substantially isostructural with Fe$_3$O$_4$, and possessing a BET surface area greater than 5 m$^2$/g and an iron-cobalt atomic ratio of 4 to 1 or above.

2. The composition of matter of claim 1 wherein said surface area is about 50 m$^2$/g or above.

3. The composition of matter of claim 2 wherein said surface area is in the range of about 100 to 300 m$^2$/g.

4. The composition of matter of claim 1 wherein said spinel is of the formula: Fe$_x$Co$_y$O$_4$, wherein x and y are integer of decimal values, other than zero, and wherein the sum of x+y is 3, and the x/y is 4:1 or above.

5. The composition of matter of claim 4 wherein the ratio: x/y is in the range of about 7:1–35:1.

6. The composition of matter of claim 5 wherein the ratio: x/y is about 19–20:1.

7. The composition of matter of claim 4 wherein said spinel is of the formula Fe$_{2.85}$Co$_{0.15}$O$_4$.

8. The composition of matter of claim 1 further comprising a mixture of said spinels in which at least two iron-cobalt spinels are present, being isostructural with Fe$_3$O$_4$, having BET surface areas greater than 5 m$^2$/g, wherein said spinels individually possess different iron-cobalt atomic ratios, being 4:1 or above.

9. The composition of matter of claim 1 wherein said promoter agent is present in about 0.1 to 10 gram-atom percent of metal ion based on the total gram-atoms of metals content.

10. The composition of matter of claim 9 wherein said promoter agent is selected from the group of carbonate, bicarbonate, organic acid salts and inorganic acid salts of Group IA and IIA metals.

11. The composition of matter of claim 10 wherein said promoter agent is potassium carbonate present in about 1 gram-atom % of the total metals gram-atom of said composition.

12. The composition of matter of claim 1 being of the formula: Fe$_{2.85}$Co$_{0.15}$O$_4$, having 1 gram-atom % potassium as potassium carbonate deposited thereon.

13. A composition of matter comprising a reduced and carbided iron-cobalt alloy, said composition being substantially isostructural with chi-Fe$_5$C$_2$, as determined by X-ray diffractometry and possessing a BET surface area of greater than 5 m$^2$/g, said composition produced by contacting, with a carbiding atmosphere for a time sufficient to produce said composition, said iron-cobalt alloy being isostructural with metallic alpha iron as determined by powder X-ray diffractometry, and possessing a BET surface area of greater than 5 m$^2$/g, wherein said alloy was produced by contacting, with a reducing atmosphere, an unsupported Group IA or IIA metal salt promoted iron-cobalt spinel, or mixture thereof, said spinel exhibiting a single phase powder X-ray diffraction pattern substantially isostructural with Fe$_3$O$_4$, and possessing a BET surface area greater than 5 m$^2$/g and an iron-cobalt atomic ratio of 4 to 1 or above.

14. The composition of matter of claim 13 wherein said surface area is greater of about 25–200 m$^2$/g.

15. The composition of matter of claim 14 wherein said surface area is about 60–150 m$^2$/g.

16. The composition of matter of claim 13 wherein said iron-cobalt atomic ratio is 4:1 or above.

17. The composition of matter of claim 16 wherein said iron-cobalt atomic ratio is in the range of about 7:1 to 35:1.

18. The composition of matter of claim 17 wherein said iron-cobalt atomic ratio is about 19-20:1.

19. The composition of matter of claim 18 wherein said iron-cobalt atomic ratio is about 19:1.

20. A composition of matter comprising a reduced and carbided iron-cobalt alloy, said composition being isostructural with $Fe_3C$, as determined by powder X-ray diffractometry, and possessing a BET surface area of greater than 5 $m^2/g$.

21. A process for producing the composition of matter of claim 1 comprising the steps of (a) evaporating a liquid solution comprising a mixture of iron and cobalt salts of at least one alpha-hydroxy aliphatic carboxylic acid, wherein the molar ratio of total moles of said acid to total moles of said iron and cobalt, taken as free metals, is about 1:1, or above, and wherein the atomic ratio of iron:cobalt, taken as the free metals in said mixture, is greater than 2 to 1, yielding an amorphous residue; (b) calcining said residue at elevated temperature for a time sufficient to yield an iron-cobalt spinel, exhibiting at least one spinel phase, isostructural with $Fe_3O_4$, as determined by powder X-ray diffractometry; and (c) impregnating the composition of (b) with an aqueous solution of a Group IA or Group IIA metal salt, followed by drying the resulting impregnate.

22. The process of claim 21 wherein said acid is selected from glycolic, malic, tartaric, or lactic acids, or mixtures thereof.

23. The process of claim 21 wherein said solution is an aqueous solution.

24. The process of claim 21 wherein the pH of said solution is 5 to 7.0.

25. The process of claim 22 wherein said acid is glycolic acid.

26. A composition of matter comprising the amorphous residue produced by the process in step (b) in claim 21.

27. A process for preparing an iron-cobalt alloy, being isostructural with metallic alpha iron as determined by powder x-ray diffractometry, and possessing a BET surface area of greater than 5 $m^2/g$, which comprises contacting an unsupported, Group IA or Group IIA metal salt promoted iron-cobalt spinel, or mixture thereof, said spinel exhibiting a single spinel phase isostructural with $Fe_3O_4$, and having a BET surface area greater than 5 $m^2/g$ and an iron-cobalt atomic ratio of 4:1 or above, with a reducing atmosphere under conditions of elevated temperature, pressure, and space velocity, for a time sufficient to substantially reduce the metal oxides of the spinel.

28. The process of claim 27 wherein said reducing atmosphere comprises hydrogen as a reducing element.

29. The process of claim 27 wherein said temperature is about 240° C. or greater.

30. The process of claim 27 wherein said so-produced iron-cobalt alloy is partially or completely treated with a carbiding atmosphere at elevated temperature.

31. The composition of matter of claim 10 wherein said promoter agent is selected from the group of inorganic salts comprising nitrates, halides and sulfates.

32. A composition of matter comprising an unsupported iron-cobalt spinel which exhibits a single phase power X-ray diffraction pattern substantially isostructural with $Fe_3O_4$ and which possesses a BET surface area greater than about 5 $m^2/g$ and an iron-cobalt atomic ratio of at least about 4 to 1, which is promoted with a promoter agent selected from the hydroxides of Group IA and IIA metals, and wherein said promoter agent is present in said composition in an amount of about 0.1 to 10 gram-atom percent of metal ion based on the total gram-atoms of metals content.

* * * * *

UNITED STATES PATENT AND TRADEMARK OFFICE
CERTIFICATE OF CORRECTION

PATENT NO. : 4,518,707

DATED : May 21, 1985

INVENTOR(S) : Stuart L. Soled, et. al.

It is certified that error appears in the above-identified patent and that said Letters Patent is hereby corrected as shown below:

In column 2, line 2, please delete therefrom the word "basic",

In column 5, line 4, please delete therefrom the word "basic".

Signed and Sealed this

Eighth Day of October 1985

[SEAL]

Attest:

Attesting Officer

DONALD J. QUIGG

Commissioner of Patents and Trademarks—Designate